(12) United States Patent
Walter et al.

(10) Patent No.: US 8,309,038 B2
(45) Date of Patent: Nov. 13, 2012

(54) DEVICE WITH WHICH A HISTOLOGICAL SECTION GENERATED ON A BLADE OF A MICROTOME CAN BE APPLIED TO A SLIDE

(75) Inventors: Roland Walter, Reilingen (DE);
Andreas Laudat, Meckesheim (DE);
Christoph Schmitt, Schriesheim (DE)

(73) Assignee: Leica Biosystems Nussloch GmbH, Nussloch, DE (US)

( * ) Notice: Subject to any disclaimer, the term of this patent is extended or adjusted under 35 U.S.C. 154(b) by 217 days.

(21) Appl. No.: 12/738,822

(22) PCT Filed: Nov. 14, 2008

(86) PCT No.: PCT/EP2008/065535
§ 371 (c)(1),
(2), (4) Date: Apr. 19, 2010

(87) PCT Pub. No.: WO2009/063039
PCT Pub. Date: May 22, 2009

(65) Prior Publication Data
US 2010/0216221 A1    Aug. 26, 2010

(30) Foreign Application Priority Data
Nov. 15, 2007 (DE) .................. 10 2007 047 797

(51) Int. Cl.
*A61B 10/00* (2006.01)
(52) U.S. Cl. ........ 422/536; 422/560; 422/563; 422/500; 422/50
(58) Field of Classification Search .. 83/13; 422/65–67, 422/50, 500, 560, 536
See application file for complete search history.

(56) References Cited

U.S. PATENT DOCUMENTS

| | | | |
|---|---|---|---|
| 3,723,226 A | 3/1973 | Pfohler | |
| 6,356,088 B1 | 3/2002 | Simon et al. | |
| 6,634,268 B1 * | 10/2003 | Guenther et al. | ............... 83/13 |
| 8,025,842 B2 * | 9/2011 | Nakajima et al. | ............. 422/65 |
| 2004/0194604 A1 | 10/2004 | Fischer | |

FOREIGN PATENT DOCUMENTS

| | | |
|---|---|---|
| DE | 1 748 387 | 7/1957 |
| DE | 20 28 898 | 12/1971 |
| DE | 25 06 255 | 9/1976 |
| DE | 197 33 195 | 2/1999 |
| DE | 203 05 494 | 9/2003 |
| DE | 10 2006 039 177 | 3/2007 |
| GB | 1 288 715 | 9/1972 |

OTHER PUBLICATIONS

International Preliminary Report on Patentability issued on Jun. 10, 2010 for PCT/EP2008/065535.
English Translation of the Written Opinion of the International Searching Authority issued for PCT/EP2008/065535.

* cited by examiner

*Primary Examiner* — Jyoti Nagpaul
(74) *Attorney, Agent, or Firm* — Schlee IP International, P.C.; Alexander R. Schlee

(57) ABSTRACT

A device for applying a histological section to a slide is described. The histological section is generated by a cutting action performed by a blade of a microtome. The device comprises a positioning device having a component that is rotatably mounted to a bearing and has a receptacle for receiving and holding the slide, wherein the positioning device is designed such that the slide received in the receptacle can be rotated about an axis of rotation of the rotatably mounted component.

20 Claims, 4 Drawing Sheets

DEVICE WITH WHICH A HISTOLOGICAL SECTION GENERATED ON A BLADE OF A MICROTOME CAN BE APPLIED TO A SLIDE

CROSS-REFERENCE TO RELATED APPLICATIONS

This application is a national phase entry based on the International Patent Application PCT/EP2008/065535 filed on Nov. 14, 2008 that claims the priority of the German patent application DE 102007047797.1 that was filed on Nov. 15, 2007. The entire content of this prior German patent application is herewith incorporated by reference.

BACKGROUND OF THE INVENTION

The present invention relates to a device for applying a histological section which can be generated on a blade of a microtome to a slide.

Microtomes have been known for a long time from the prior art. Thin histological sections of tissue samples embedded in paraffin are produced with them. One histological section each is applied to a slide. The slides with the histological sections are usually subjected to a further treatment, the histological sections being stained by means of a staining method in order to be finally observed with the microscope.

When a thin histological section has been prepared with the microtome, it is usually manually placed by the operator in a heated water bath. Merely exemplarily, reference is made to the document DE 203 05 494 U1 from which this proceeding at a correspondingly designed microtome is known. In the water bath the histological section experiences a stretching and smoothing so that it does not show any folds, waves or other forms of unevenness. Afterwards, the operator manually picks up the histological section swimming on the water surface of the water bath on a slide in that a part of the slide is positioned below the water surface under a suitable angle and is brought closer to the histological section swimming on the water surface, which is finally placed on the slide. When proceeding like this, there is the risk of a contamination of the water bath and thus of the various histological sections which swim in the water bath one after the other. For avoiding such contamination the water bath would often have to be replaced. Moreover, this proceeding requires considerable skill of the operator in order to guarantee a constant quality standard of the preparation or, respectively, during the application of the histological section to the slide.

An alternative approach provides that a so-called adhesive tape is manually applied to the tissue block to be cut prior to the preparation of the histological section. As a result thereof, compression or tearing of the histological section during the cutting operation is prevented. The adhesive tape with the histological section is then applied to the slide with the histological section side. Under the effect of UV light, the adhesive bond between the adhesive tape and the histological section is dissolved so that only the histological section is applied to the slide or, respectively remains on the slide. This application operation, too, involves high manual expense and requires a post-treatment by UV light. In addition, only after removing the adhesive tape, the quality of the histological section can be assessed.

Further, the document DE 20 28 898 discloses a device for the automatic removal of a histological section from a blade of a microtome.

SUMMARY OF THE INVENTION

The present invention is thus based on the object to reduce the manual expense to be rendered by an operator during the application of a histological section to a slide and to preferably achieve a high quality standard during the application operation.

The inventive device of the type mentioned at the beginning solves the above object by a device for applying a histological section generated on a blade of a microtome to a slide, comprising a positioning device having a component that is rotatably mounted to a bearing and has a receptacle for receiving and holding the slide, wherein the positioning device is designed such that the slide received in the receptacle can be rotated about an axis of rotation of the rotatably mounted component. Accordingly, such a device comprises a positioning device. A histological section generated with the microtome is positioned on the blade or, respectively, on the blade holder. With the positioning device, the slide can be moved from an initial position into an application position. In the application position of the slide, the histological section positioned on the blade holder can at least in part be brought into contact with the surface of the slide. As a result thereof, the histological section can be applied to the slide.

DETAILED DESCRIPTION OF THE INVENTION

According to the invention, it has at first been recognized that the application operation of a histological section to a slide can be considerably simplified when, in a manner according to the invention, a positioning device is provided with which the slide can be suitably positioned so that the histological section is brought into contact with the surface of the slide. Due to the adhesive force between the histological section and the slide, the histological section adheres to the slide, thus is applied to the slide as a result thereof and can then be fed to the further histological treatment. Therefore, with the positioning device the slide can be positioned in a simple and reproducible manner at the histological section or, respectively, at the blade or, respectively, at the blade holder of the microtome. This can take place manually or automatically. In any case, according to the invention the histological section is applied to or on the slide immediately after preparing the histological section with the microtome.

As already indicated, the histological section could be manually applied with the device according to the invention. For example, an actuating lever could be provided with which the positioning device can be manually operated by an operator to move the slide from the initial position into the application position in order to hereby apply the histological section to the slide. Preferably, however, it is provided that the histological section can be automatically applied to the slide. For this purpose, a motor, in particular a stepper motor or a direct current motor could be provided which drives the positioning device in order to move the slide from the initial position into the application position.

Basically, the slide can be moved with a translatory motion along a substantially linear direction to the histological section or, respectively, to the blade holder in order to be brought into contact with the histological section. According to a preferred embodiment, the slide can be moved from the initial position into the application position by means of a rotary motion or a swivel motion. According to this embodiment, the substantially elongated slide can be brought closer to the blade holder or, respectively, to the histological section on its one end with respect to its longitudinal direction by means of a rotary motion or a pivot motion.

The positioning device could thus have a gripper arm or a robot arm. A slide is then moved into the application position with the gripper arm or the robot arm. The movement of the slide can comprise a translatory motion and/or a rotary and/or a swivel motion. In other words, with a gripper arm or a robot arm a complex slide motion for bringing the slide into contact with the histological section can be implemented in a reproducible manner.

According to a particularly preferred embodiment the positioning device has a rotatably mounted component, the rotatably mounted component having a receptacle for the slide. Preferably, the slide can be fixed to the rotatably mounted component with the receptacle. The receptacle could be designed in the form of a slot into which one end of the slide is inserted. Clamping means could be provided on the receptacle with which the slide can be fixed in the receptacle and on the rotatably mounted component.

Preferably, the rotatably mounted component is rotatably mounted in a plain bearing. The rotatably mounted component could, for example, have a cylindrical shape, the cylinder shell of the rotatably mounted component serving as the rotatable part of the plain bearing. Alternatively or additionally, the rotatably mounted component could be put into rotation by means of a motor. For this purpose, an electric motor could be connected to the rotatably mounted component directly or indirectly via a corresponding transmission in order to put the rotatably mounted component into rotation given a corresponding activation of the electric motor. Possibly, mechanical end stops could be provided which limit the rotation of the rotatably mounted component, for example towards the application position.

According to a preferred embodiment, the axis of rotation of the rotatably mounted component is oriented substantially parallel to the blade's cutting edge. When the slide is rotated or swiveled towards the blade holder with the aid of the rotatably mounted component about the axis of rotation which is oriented substantially parallel to the blade's cutting edge, the slide approaches—at least with respect to a direction of the surface of the slide which corresponds to the direction of the axis of rotation—the blade holder in a uniform manner and can be effectively brought into contact with the histological section positioned on the blade holder. The rotatably mounted component could be arranged in front of the microtome and below the knife blade or, respectively, the knife holder, for example between the microtome and an operator actuating the microtome. Alternatively and in particular additionally thereto, the axis of rotation of the rotatably mounted component could lie in a plane which is oriented substantially identically or parallel to the surface of the blade holder. Such an orientation or arrangement of the axis of rotation of the rotatably mounted component can likewise allow a uniform approach of the slide to the blade holder and thus to the histological section positioned on the blade holder. As a result thereof, in particular the side of the slide facing the histological section, in an area near the application position, can be brought closer to the surface of the blade holder in a substantially parallel manner. According to this alternative, for example, the rotatably mounted component could be arranged to the left or the right of the knife holder and thus not directly between the microtome and the operator.

According to a most particularly preferred embodiment, a pipetting device is provided with which a predeterminable amount of liquid can be applied to the slide. As a predeterminable amount of liquid, one or more liquid drops can be provided. The pipetting device could be arranged and designed such that the liquid can be applied to the slide in the initial position. Liquid could be applied to the slide already before the application of the histological section or, respectively, the slide could be wetted with liquid. Preferably, however, it is provided to apply the liquid to the slide with the pipetting device after the application operation of the histological section to the slide such that at least a part of the liquid spreads between the histological section and the surface of the slide. For this, the place of application of the liquid could be in an area of the slide surface which is not covered by the histological section, but which is not too far from the histological section. Specifically, the place of application of the liquid could be in a marginal area of the histological section. Spreading of the liquid between the histological section and the slide surface takes place, for example, due to capillary forces. An area-wide liquid film is formed. On this liquid film, the histological section can "swim" in a manner comparable to the water bath according to document DE 203 05 494 U1 or slightly move on the slide.

The liquid could consist of water or the liquid could comprise a mixture of alcohol and water. The water could be distilled water. However, chemicals or minerals which favor the uniform spreading or wetting operation of the liquid on the slide or between the histological section and the surface of the slide could be added to the water or, respectively, the alcohol.

According to a most particularly preferred embodiment, a heating device is provided with which the slide can be heated with a predeterminable temperature for a predeterminable period of time or a predeterminable time-varying temperature curve. As a result thereof, the histological section swimming on the liquid film can stretch on the slide or be stretched hereby. An effect comparable to the water bath can likewise be achieved hereby. Preferably, the slide is heated in the initial position at the heating device with the predeterminable temperature or, respectively the temperature curve. Thus, the slide could, for example, be heated with a constant temperature for three seconds. Alternatively, however, a time-varying temperature curve is likewise conceivable according to which the slide can be brought—with a linear temperature increase—from room temperature to a predeterminable temperature value, this predeterminable temperature value is kept substantially constant for a duration of approx. 2 to 5 seconds and thereafter is again brought to room temperature. The heating device could have a Peltier element or an infrared heat source.

Preferably, the heating device could have a closed-loop control system with which the predeterminable temperature or the predeterminable time-varying temperature curve can be controlled. For this purpose, a temperature sensor could be provided in immediate proximity to the slide, with which the currently prevailing temperature—the actual value—is measured and the value can be transferred to a control unit of the closed-loop control system. With the control unit, the actual value is then compared to a desired value, and the heating device is controlled accordingly in order to adjust the actual value to the desired value as exactly as possible.

So that the prepared histological section adheres to the slide when it is brought into contact with the slide and does not stick to the blade holder or to the blade, preferably the surface of the blade holder and/or the surface of the blade at least in part has a coating with a low friction coefficient and/or a non-stick coating. Such a coating could, for example, be formed of a Teflon coating. A suitable treatment of the surface of the blade holder and/or the surface of the blade, for example, by polishing the surface, could also be provided and could result in a low friction coefficient.

Most particularly preferred, the slide comprises glass or plastic. Specifically, it could be a conventional slide as used in microscopy and in particular in pathological microscopy. Insofar, the histological section is directly applied to the slide, with which the histological section—usually after further processing steps such as staining—is examined with the microscope.

Further, the slide could have a coating which favors the application operation of the histological section. Such a coating could be formed by a liquid applied with the pipetting device before the application operation. The slide could, however, also be provided with a coating formed of chemicals. Basically, the surface property or, respectively, the coating of the slide should be designed such that after bringing the slide into contact with the histological section positioned on the blade holder the histological section can be applied on or to the slide, and if a liquid is applied to the slide with the pipetting device after the application operation, the liquid can preferably spread between the surface of the slide and the histological section.

Most particularly preferred, the histological section can be applied to the slide due to adhesive force between the histological section and the surface of the slide. This can, for example, be achieved by a suitable selection of the coating of the surface of the blade holder and/or the surface of the blade and/or the surface of the slide. In particular, when the adhesiveness of the surface of the blade holder is less than the adhesiveness of the surface of the slide, the application operation of the histological section to the slide is favored as a result thereof.

With the device according to the invention the application operation of the histological section to the slide can be automated. According to a preferred embodiment, a feed device is provided for this purpose, with which slides on which one histological section each is to be applied can be fed to the device. Such a feed device could, for example, be designed in the form of a transport belt which sequentially feeds several slides to the device and in particular to the rotatably mounted component.

In a comparable manner, a take-away device could be provided for taking away slides on which one histological section each has been applied. The take-away device could be designed in the form of a transport belt as well. Insofar, the application operation of the histological section onto a slide after a cutting operation with the microtome manually initiated by an operator can be largely automated in an advantageous manner. Preferably, it is provided that the histological section can be automatically prepared with the microtome. When in this case both a feed device and a take-away device are provided with which slides can each time be fed to the inventive device or, respectively, taken away from the device according to the invention, the application operation of histological sections to slides on the microtome can be fully automated. For monitoring the automatic application operation at least one sensor and/or at least one camera can be provided with which the cutting operation with the microtome on the one hand and the positioning of the slide with the positioning device on the other hand can be monitored.

With the microtome a histological section is prepared which is positioned on the blade or on the blade holder. With a positioning device the slide is moved from an initial position into an application position. In the application position of the slide, the histological section positioned on the blade holder is, at least in part, brought into contact with the surface of the slide. As a result thereof, the histological section is applied to the slide.

For the application of histological sections on slides, at least one, preferably all of the method steps mentioned below—in particular in the order listed—are provided:

the histological section is automatically applied to the slide, the slide is moved from the initial position to the application position by means of a rotary motion or a swivel motion in order to apply the histological section to the slide, after the application of the histological section to the slide, the slide is moved from the application position back into the initial position, a predeterminable amount of liquid is applied to the slide with a pipetting device, preferably in the initial position (this can take place before or after the application of the histological section to the slide), with the pipetting device, the liquid is applied to the slide such that at least a part of the liquid spreads between the histological section applied to the slide and the surface of the slide, with a heating device, the slide—preferably in the initial position—is heated with a predeterminable temperature or a predeterminable time-varying temperature curve, with a feed device, the slides to which one histological section is to be applied are fed to the device, and with a take-away device, the slides to which one histological section each has been applied are taken away from the device.

The automatically performed method steps can be monitored with at least one sensor and/or at least one camera (in particular a CCD camera). For this purpose, a corresponding control device can be provided which evaluates signals from a sensor or, respectively, the images of a camera and activates or controls the corresponding actuators of the positioning device, the pipetting device, the heating device, the feed device and/or the take-away device.

There are now different possibilities of designing and developing the teaching of the present invention in an advantageous manner. Reference is made on the one hand to the claims which are dependent on claim 1 and on the other hand to the following description of the preferred embodiments of the invention with reference to the drawing. In connection with the description of the preferred embodiments of the invention with reference to the drawing, also generally preferred embodiments and developments of the teaching are described. In the drawing, each Figure is a schematic illustration.

DETAILED DESCRIPTION OF THE DRAWINGS

Figure 1:
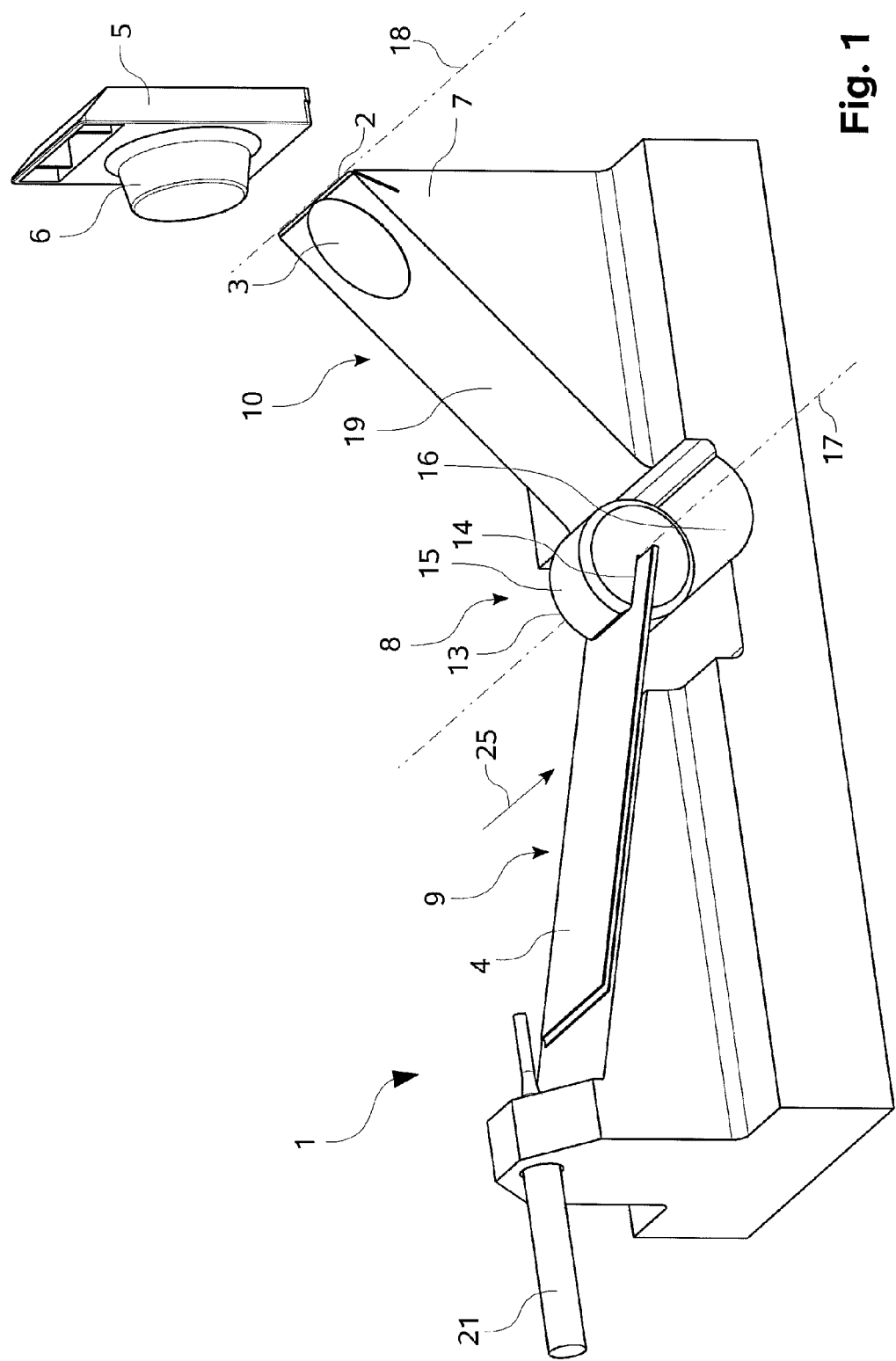
FIG. 1 is a perspective view of an embodiment of an inventive device for applying a histological section which can be generated on a blade of a microtome to a slide.

In the Figures, identical or similar component parts are identified with the same reference signs. FIG. 1 shows an inventive device 1 for applying a histological section 3 generated on a blade 2 and positioned thereat to a slide 4. The histological section 3 has been prepared with the aid of a microtome which, as such, is not completely shown in the Figures. Merely the cassette 5 which is clamped into the (not shown) microtome is shown in the Figures with the tissue block 6 fixed thereto. The microtome concerned is a rotation microtome with which the cassette 5 and the tissue block 6 are moved together in vertical direction relative to the blade 2. Here, the blade 2 is stationarily fixed on the blade holder 7. Accordingly, the cassette 5 and the tissue block 6 were moved downward in vertical direction at least once and back into the position shown in FIG. 1 in order to prepare the histological section 3 shown in FIG. 1.

Figure 2:
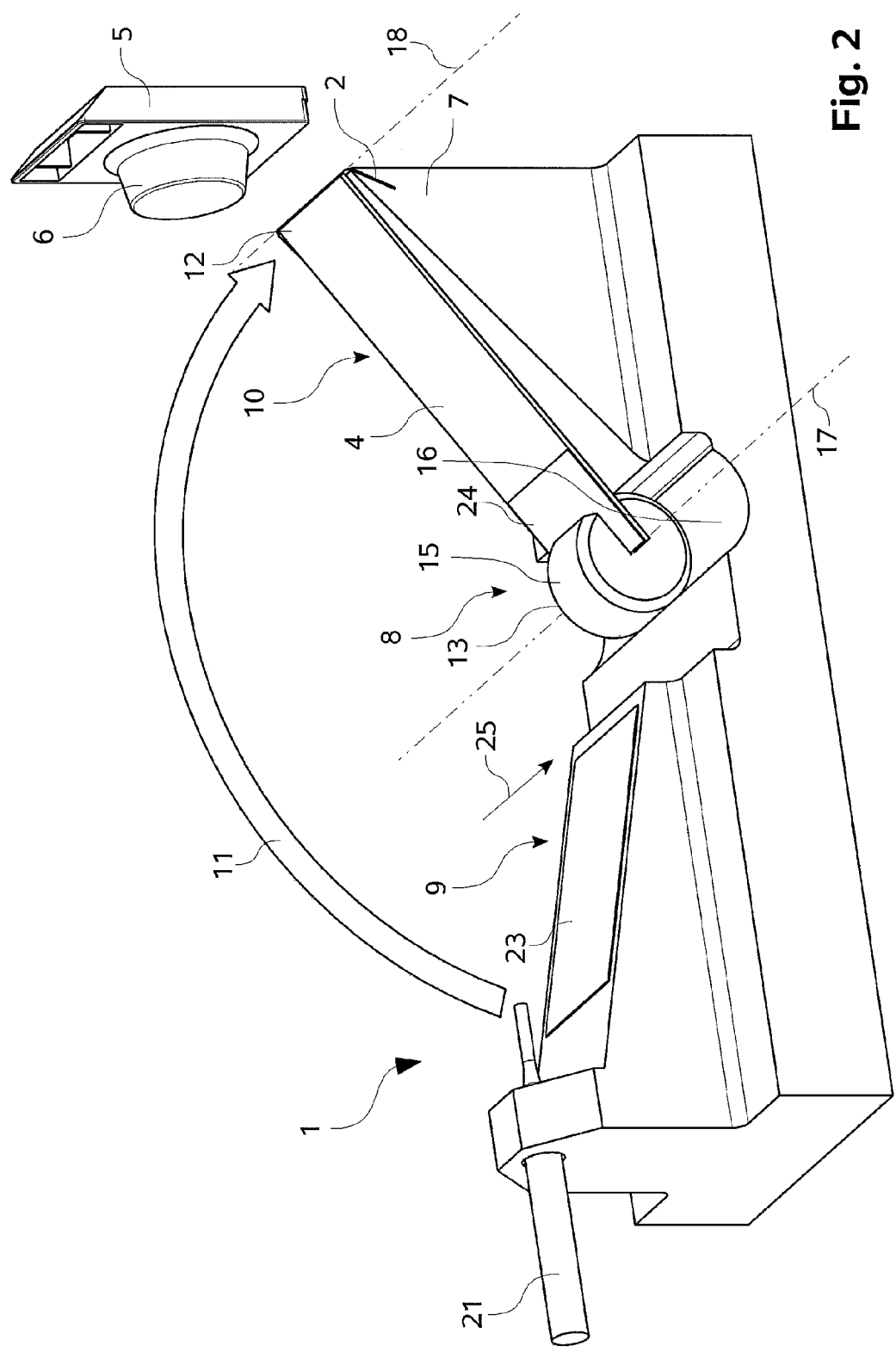
FIG. 2 shows the device from FIG. 1 in another operating state.

The inventive device 1 comprises a positioning device 8 with which the slide 4 can be brought from the initial position 9 shown in FIG. 1 into an application position 10 shown in FIG. 2. The slide 4 is brought from the initial position 9 into the application position 10 with the positioning device 8 by means of a rotary motion. In FIG. 2, this is indicated by the arrow 11. In this operating state of the inventive device 1, the histological section 3 not visible in FIG. 2 is located between the slide 4 and the blade holder 7. In this position of the slide 4, the end region 12 of the slide 4 can be brought into contact with the histological section 3. As a result thereof, the histological section 3 can be applied to the slide 4 in a manner according to the invention.

The positioning device 8 has a rotatably mounted component 13 with which the slide 4 can be brought from the initial position 9 into the application position 10 and back into the initial position 9. The rotatably mounted component 13 comprises a receptacle 14 with which the slide 4 can be fixed—for the positioning operation—by the rotatably mounted component 13. The rotatably mounted component 13 is designed substantially cylindrically and is rotatably mounted in a plain bearing. The shell 15 of the rotatably mounted component 13 represents the rotatable part of the plain bearing. The cylindrical shell surface 16 represents the stationary part of the plain bearing and is connected to the blade holder 7. The rotatably mounted component 13 is automatically rotated by a motor not shown in the Figures so that the slide 4 can be moved between the initial position 9 and the application position 10.

The axis of rotation 17 of the rotatably mounted component 13 is oriented parallel to the cutting edge of the blade 2. The extension of the cutting edge of the blade 2 is indicated in broken lines in the Figures and is identified by the reference sign 18. The axis of rotation 17 of the rotatably mounted component 13 is further arranged in a plane which is arranged parallel to the surface 19 of the knife holder 7. The histological section 3 is positioned on the surface 19 of the knife holder 7 after a cutting operation, see FIG. 1. By way of the arrangement of the axis of rotation 17 of the rotatably mounted component 13, it can thus be achieved that the slide 4 with its end region 12 uniformly approaches the surface 19 of the knife holder 7 or, respectively, the histological section 3 when approaching the application position 10, and does not approach the surface 19 of the knife holder 7 with the left or right longitudinal edge of the slide 4 (wedged or, respectively, tilted).

Figure 3:
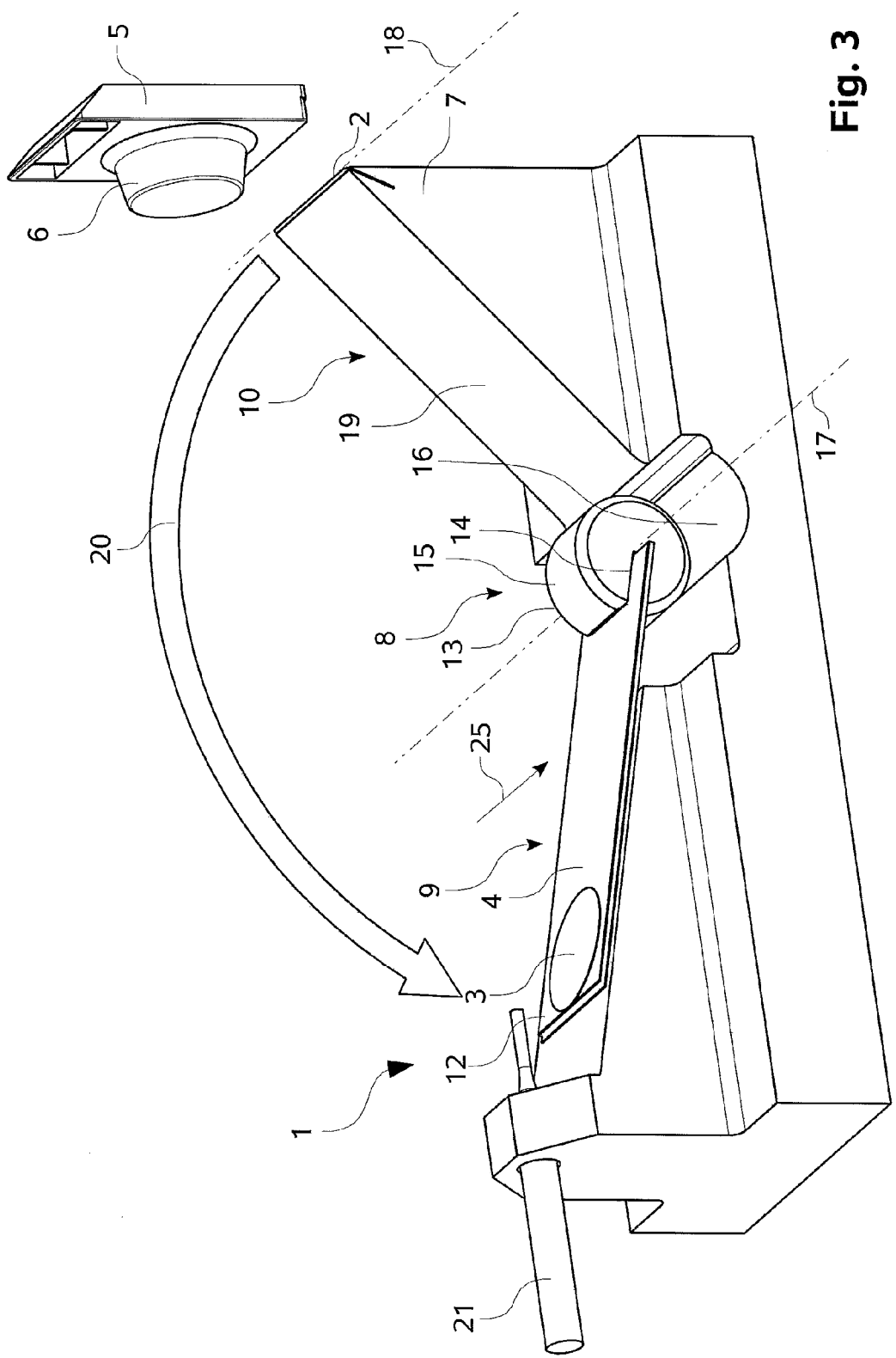
FIG. 3 shows the device from FIGS. 1 and 2 in a further operating state.

The application operation of the histological section 3 to the slide 4 by means of the device 1 shown in the Figures proceeds as follows:

A slide 4 is placed in the receptacle 14 of the rotatably mounted component 13 in the initial position 9. With the microtome, a histological section 3 is prepared which is positioned on the surface 19 of the blade holder 7, see FIG. 1. With the rotatably mounted component 13, the slide 4 is moved into the application position 10 according to the arrow 11 from FIG. 2. Thereat, the histological section 3 comes into contact with the slide 4 and adheres on the slide 4. The slide 4 together with the histological section 3 is moved back into the initial position 9 with the aid of the rotatably mounted component 13 according to the arrow 20 from FIG. 3. In doing so, the mere mechanical application operation of the histological section 3 to the slide 4 is completed. Nevertheless, a further processing step takes place which can basically still be attributed to the application operation of the histological section 3 to the slide 4.

Figure 4:
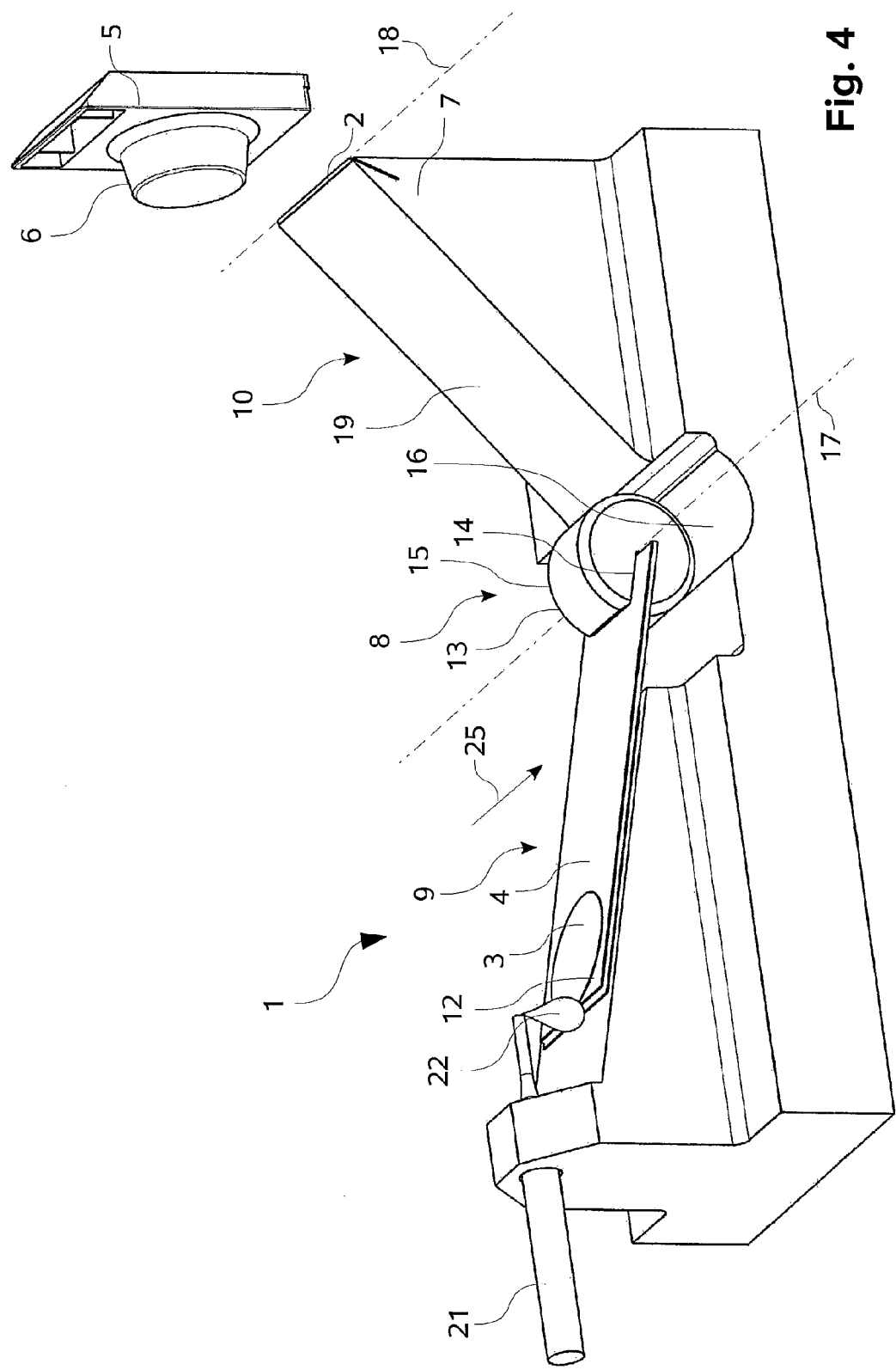
FIG. 4 shows the device from FIGS. 1 to 3, liquid being applied to the slide.

With the aid of the pipetting device 21, a predeterminable amount of liquid 22 can be applied to the slide 4. The liquid is applied to the slide 4 when the slide 4 is again in the initial position 9. This is indicated in FIG. 4. The liquid 22 comprises a mixture of alcohol and water. With the aid of the pipetting device 21, the liquid 22 is applied to the end region 12 of the slide so that the liquid 22 can spread between the histological section 3 and the slide 4 due to capillary forces. This operation is accompanied, or respectively, supported by heating the slide 4, which takes place with the aid of the heating device 23. The heating device 23 is integrated in that part of the device 1 which is located directly below the application position 9. The heating device 23 has a Peltier element, which is, for example, shown in FIG. 2. The heating operation of the slide 4 is controlled with a control unit not shown in the Figures. To this end, temperature sensors which are likewise not shown in the Figures are provided in immediate proximity to the application position 9 of the slide 4. With the heating device 23, the slide 4 and thus also the histological section 3 can be heated with a predeterminable temperature over a predeterminable period of time. As the liquid 22 spreads between the histological section 3 and the surface of the slide 4 and is heated by the heating device 23, the histological section 3 can slightly move on the slide 4 also after the mere mechanical application operation. As a result thereof, an undesired slight unevenness of the histological section 3 can advantageously be compensated or, respectively, removed.

The slide 4 consists of glass and has an area 24 which is provided with patient data and data of the cassette 5 on the tissue block 6. In the Figures, neither a feed device nor a take-away device are shown with which slides 4 can be supplied to or, respectively, taken-away from the device 1. Nevertheless, slides 4 could be fed with a feed device from an area behind the receptacle 14 of the rotatably mounted component 13 shown in FIG. 1 along the direction identified with the arrow 25. Slides 4, to each of which one histological section 3 has been applied, could be taken away with a take-away device into a front area shown in FIG. 1 in a direction in the extension of the arrow 25. The feeding or, respectively, the taking away of the slides 4 could likewise take place automatically.

Finally, it is most particularly pointed out that the above discussed embodiments merely serve to describe the claimed teaching but do not restrict the teaching to the embodiments.

LIST OF REFERENCE SIGNS 1 device
2 blade
3 histological section
4 slide
5 cassette
6 tissue block from which (3) is prepared
7 blade holder
8 positioning device
9 initial position
10 application position
11 arrow
12 end region of (4), which can be brought into contact with (3)
13 rotatably mounted component
14 receptacle for (4) of (13)
15 shell of (13)

16 cylindrical shell surface of (13)
17 axis of rotation of (13)
18 extension of the cutting edge of the blade
19 surface of (7) on which (3) is positioned
20 arrow
21 pipetting device
22 liquid
23 heating device
24 area of (4) provided with data
25 arrow

What is claimed is:

1. A device for applying histological sections generated on a blade of a microtome to slides, the device comprising:
    a positioning device having a component that is rotatably mounted to a bearing and has a slide receptacle for receiving and holding a slide, wherein
    the positioning device is designed such that the slide receptacle and with it a slide when received in the slide receptacle can be rotated about an axis of rotation of the rotatably mounted component.

2. The device according to claim 1, comprising means for automatically applying the histological section to the slide.

3. The device according to claim 1, comprising means for moving the slide from an initial position to an application position by at least one of a rotary motion and a swivel motion.

4. The device according to claim 1, wherein the positioning device has at least one of a gripper arm and a robot arm for moving a slide into the application position.

5. The device according to claim 1, wherein the receptacle for the slide is adapted to fix the slide to the rotatably mounted component.

6. The device according to claim 5, wherein the rotatably mounted component is at least one of rotatably mounted in a plain bearing and rotatable by means of a motor.

7. The device according to claim 5, wherein the axis of rotation of the rotatably mounted component extends one of substantially in parallel to a cutting edge of the blade, in a plane that substantially coincides with a surface of the blade holder, and in parallel to a surface of the blade holder.

8. The device according to claim 1, further comprising a pipetting device for applying a predeterminable amount of liquid to the slide.

9. The device according to claim 8, comprising means for applying the liquid to the slide with the pipetting device such that at least a part of the liquid spreads between the histological section applied to the slide and the surface of the slide.

10. The device according to claim 8, wherein the liquid is at least one of water and a mixture of alcohol and water.

11. The device according to claim 8, wherein the pipetting device is adapted to apply the liquid in the initial position of the slide.

12. The device according to claim 1, further comprising a heating device that is adapted to heat the slide with a predeterminable temperature over a predeterminable period of time or a predeterminable variable temperature as a function over time.

13. The device according to claim 12, wherein the heating device comprises at least one of a Peltier element and an infrared heat source.

14. The device according to claim 12, wherein the heating device comprises a closed loop control system controlling the predeterminable temperature or the predeterminable variable temperature as a function over time.

15. The device according to claim 1, wherein at least one of the surface of the blade holder and the surface of the blade are at least in part coated with at least one of a low friction coefficient coating and a non-sticking coating.

16. The device according to claim 1, wherein the slide comprises at least one of a glass coating, a plastic coating, and a coating facilitating the application of the histological section.

17. The device according to claim 1, comprising means for applying the histological section to the slide by adhesive forces between the histological section and the surface of the slide.

18. The device according to claim 1, further comprising a feed device feeding slides that are adapted to receive one histological section each to the device.

19. The device according to claim 1, wherein a removing device is provided carrying away those slides from the device to which one histological section each has been applied.

20. The device according to claim 1, wherein the histological section can be generated by one of automatically by means of the microtome and manually by an operator.

* * * * *